United States Patent
Booth

(10) Patent No.: US 9,199,051 B2
(45) Date of Patent: Dec. 1, 2015

(54) SYSTEM AND METHOD FOR FACILITATING AN INTUBATION

(71) Applicant: Anton Booth, Coorparoo (AU)

(72) Inventor: Anton Booth, Coorparoo (AU)

( * ) Notice: Subject to any disclaimer, the term of this patent is extended or adjusted under 35 U.S.C. 154(b) by 0 days.

(21) Appl. No.: 14/309,509

(22) Filed: Jun. 19, 2014

(65) Prior Publication Data

US 2015/0224273 A1 Aug. 13, 2015

Related U.S. Application Data

(60) Provisional application No. 61/939,224, filed on Feb. 12, 2014.

(51) Int. Cl.
*A61B 1/267* (2006.01)
*A61M 16/04* (2006.01)
*A61B 1/04* (2006.01)

(52) U.S. Cl.
CPC .............. *A61M 16/0488* (2013.01); *A61B 1/04* (2013.01); *A61B 1/267* (2013.01)

(58) Field of Classification Search
CPC .......................... A61M 16/04; A61M 16/0418
USPC ...................................... 128/200.26; 600/194
See application file for complete search history.

(56) References Cited

U.S. PATENT DOCUMENTS

| | | | |
|---|---|---|---|
| 4,529,400 A | 7/1985 | Scholten | |
| 4,622,965 A | 11/1986 | Teeple | |
| 4,659,328 A | 4/1987 | Potter et al. | |
| 4,949,716 A | 8/1990 | Chenoweth | |
| 5,038,766 A * | 8/1991 | Parker | 128/200.26 |
| 5,174,283 A * | 12/1992 | Parker | 128/200.26 |
| 5,259,377 A * | 11/1993 | Schroeder | 128/207.14 |
| 5,327,881 A * | 7/1994 | Greene | A61B 1/2676 600/120 |
| 5,791,338 A * | 8/1998 | Merchant et al. | 128/200.26 |
| 6,623,449 B2 | 9/2003 | Paskar | |
| 6,830,049 B2 * | 12/2004 | Augustine et al. | 128/207.15 |
| 8,475,364 B2 | 7/2013 | Supiez | |
| 2002/0096177 A1* | 7/2002 | Toti et al. | 128/207.15 |
| 2004/0059257 A1 | 3/2004 | Gaber | |
| 2007/0028923 A1* | 2/2007 | Souris et al. | 128/207.15 |
| 2009/0090357 A1* | 4/2009 | Schwartz et al. | 128/200.26 |
| 2011/0120458 A1* | 5/2011 | Schwartz et al. | 128/200.26 |
| 2011/0263935 A1* | 10/2011 | Qiu | 600/109 |
| 2011/0265789 A1 | 11/2011 | Gabriel | |
| 2012/0073572 A1 | 3/2012 | Li | |
| 2012/0078050 A1 | 3/2012 | Schwartz et al. | |
| 2012/0078055 A1* | 3/2012 | Berci | A61B 1/0005 600/188 |
| 2012/0178999 A1* | 7/2012 | Takeda et al. | 600/188 |
| 2013/0255671 A1 | 10/2013 | Furman et al. | |

(Continued)

FOREIGN PATENT DOCUMENTS

| | | |
|---|---|---|
| WO | WO 2005/070489 A | 8/2005 |
| WO | WO 2007/138569 A2 | 12/2007 |
| WO | WO 2011/119521 A1 | 9/2011 |

OTHER PUBLICATIONS

International Search Report and Written Opinion for PCT/AU2015/050047, mailed on Apr. 7, 2015.

*Primary Examiner* — Nicholas Lucchesi
*Assistant Examiner* — Gerald Landry, II

(57) ABSTRACT

A device for use with an endotracheal tube. The device includes a shaft having a wall with a flexible region proximate a tip of the shaft. The shaft both distally and proximally of the flexible region is of a higher durometer than the durometer of the flexible region.

38 Claims, 11 Drawing Sheets

(56) References Cited

U.S. PATENT DOCUMENTS

| | | | |
|---|---|---|---|
| 2014/0041665 A1* | 2/2014 | Hwang | A61M 16/04 128/207.15 |
| 2014/0128681 A1* | 5/2014 | Fordinal | 600/194 |
| 2014/0275778 A1* | 9/2014 | Gunday | A61M 16/0488 600/109 |

* cited by examiner

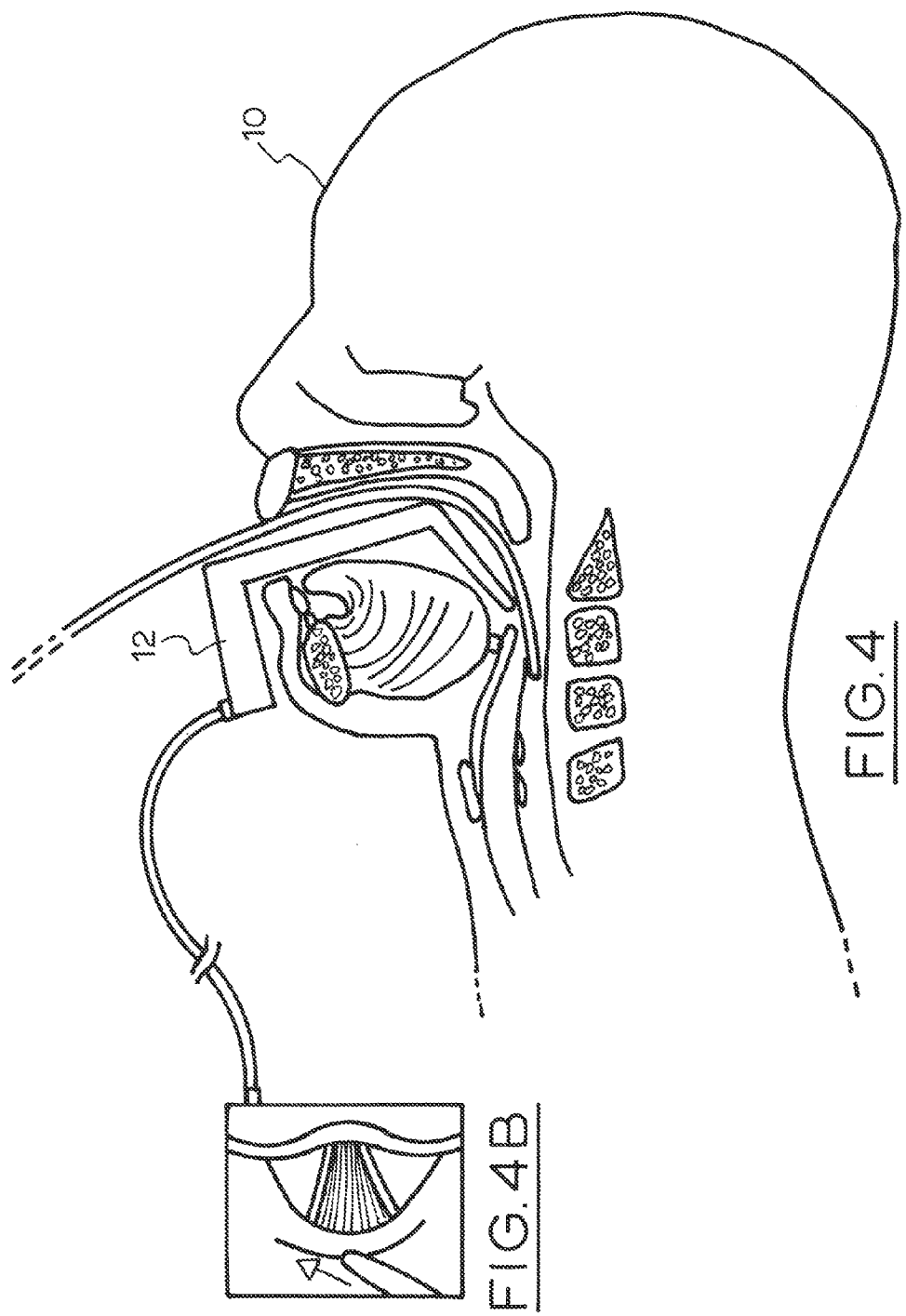

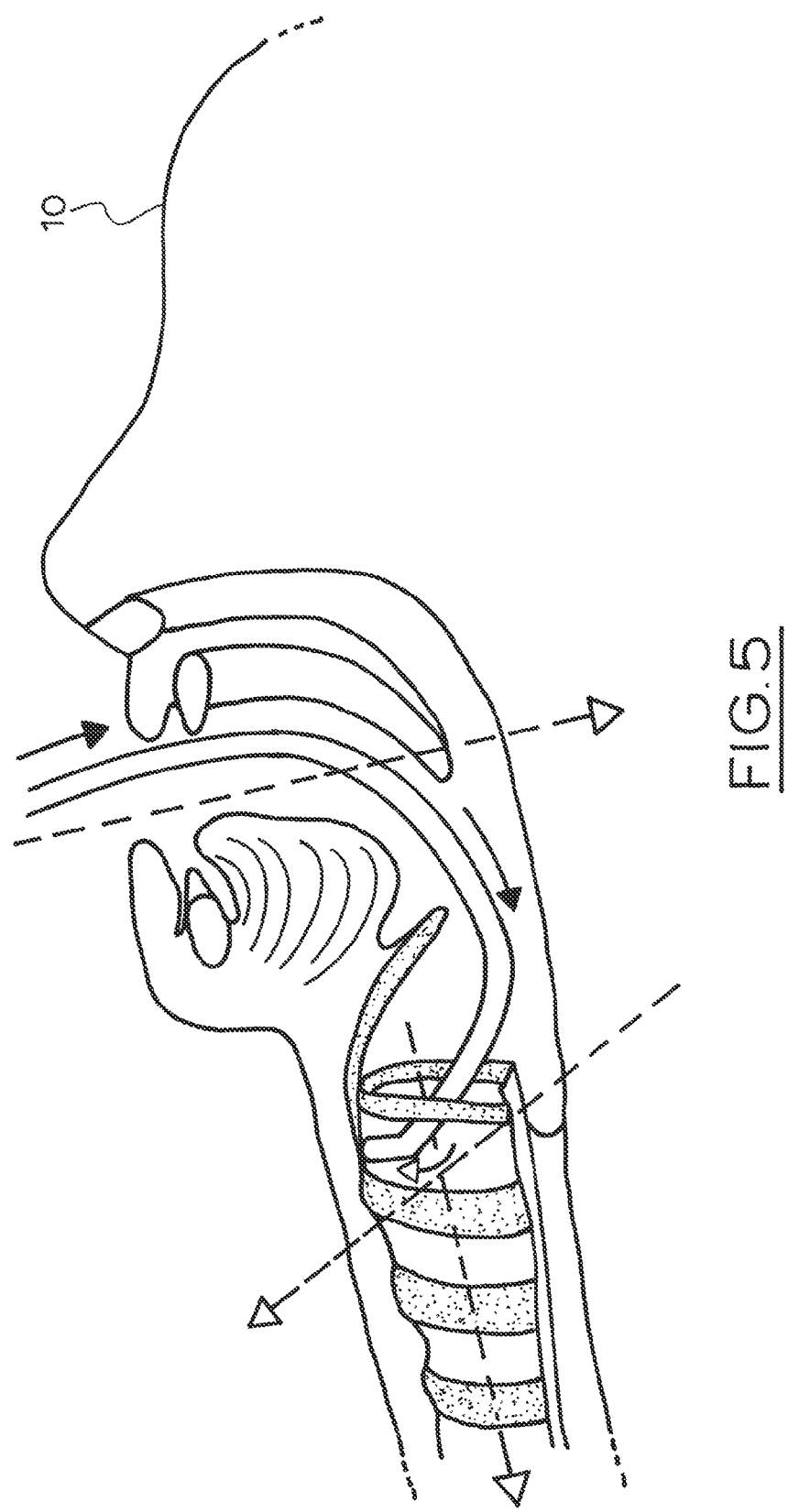

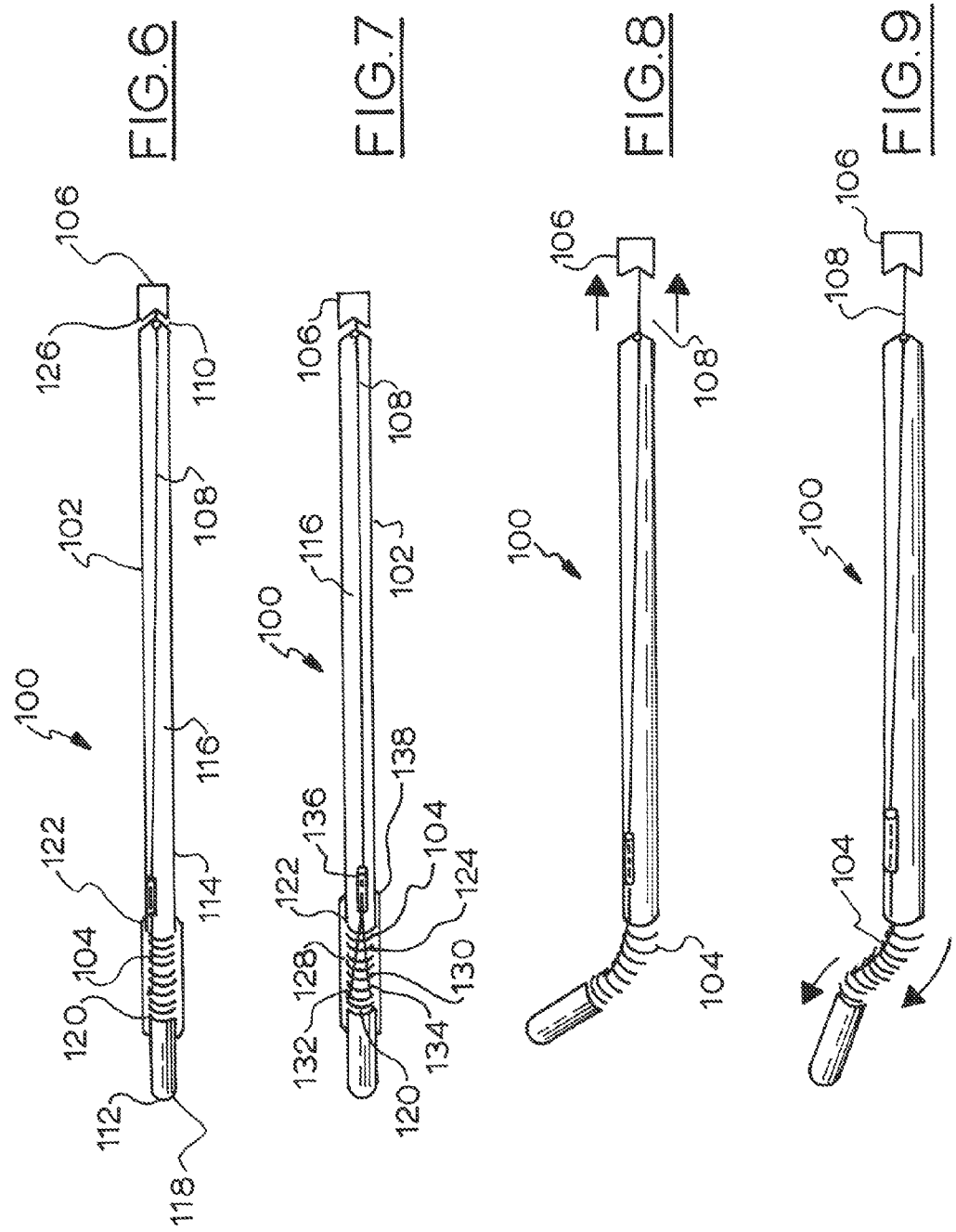

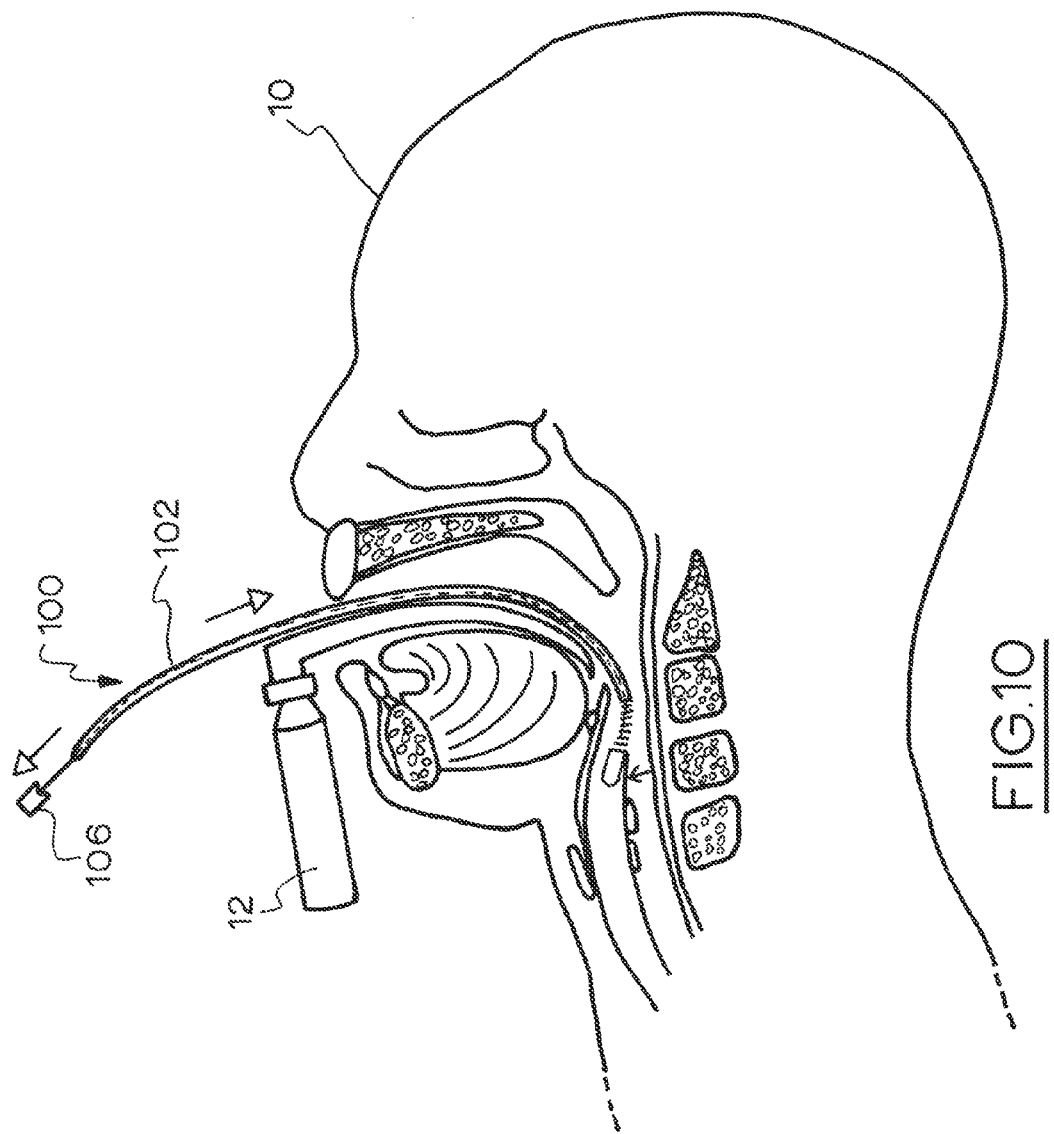

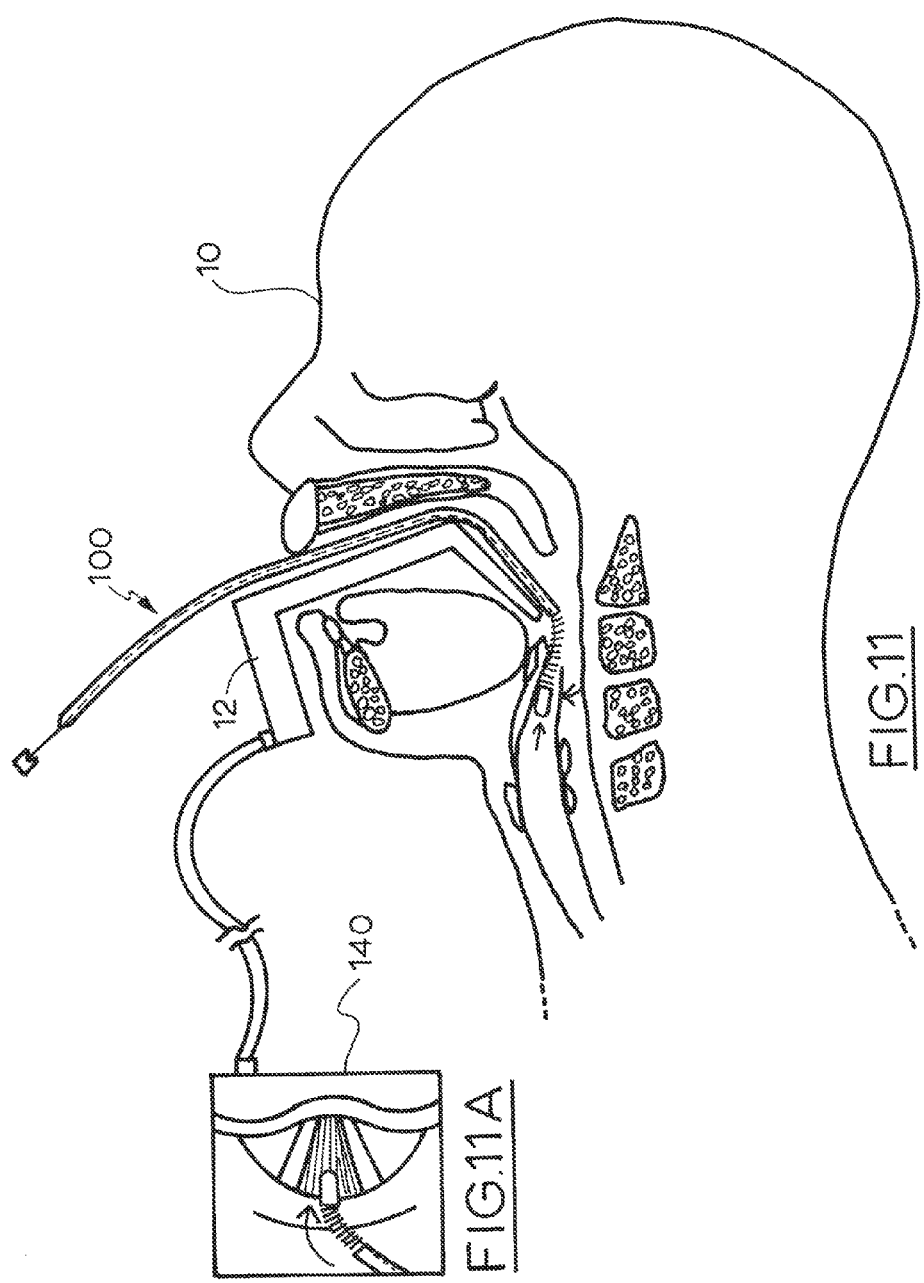

SYSTEM AND METHOD FOR FACILITATING AN INTUBATION

CROSS-REFERENCE TO RELATED APPLICATION

This application claims priority under 35 U.S.C. §119(e) to provisional U.S. patent application No. 61/939,224, entitled "System and Method for Facilitating an Intubation," filed Feb. 12, 2014.

FIELD OF THE INVENTION

The present invention relates to improvements in devices designed to facilitate an intubation procedure, such as placement of an endotracheal tube.

BACKGROUND OF THE INVENTION

Endotracheal intubation is a core technique in anaesthesia (and critical care medicine). It is the gold standard method to provide oxygenation and ventilation to a patient under general anaesthesia. It requires the passage of an endotracheal tube (ETT) through the vocal cords into the trachea.

The primary and traditional method of endotracheal intubation involves direct laryngoscopy with a laryngoscope. The laryngoscope has a gently curved blade which is passed into the mouth and sits in the oropharynx to provide a direct line of sight to the vocal cords. Most patients can be successfully intubated using this technique; however circumstances where this is difficult or impossible occur relatively regularly in anaesthesia (6%) and other areas of critical care (16%).

Difficult intubation has the potential to result in great patient harm from inadequate oxygenation causing death, brain damage and/or heart attacks. Difficult intubation requiring multiple or repeated attempts can also result in trauma to the airway. Management of these scenarios has been and continues to be a major focus in anaesthesia and critical care medicine. This has resulted in multiple "airway" management strategies and the development of improved equipment.

Although there can be a variety of causes that result in a difficult intubation, ultimately there are two main factors that are responsible:

Difficulty in visualising the vocal cords and/or

Difficulty in directing an ETT through the vocal cords into the trachea.

These two factors are generally managed by using a videolaryngoscope (to improve visualisation of the vocal cords) and/or a specialised ETT introducer (to guide the ETT through the vocal cords). However both of these techniques have limitations which can still result in a difficult or failed intubation for various reasons detailed below.

For the first factor, difficult visualisation, direct laryngoscopy relies on achieving a "line of sight" to directly visualise the vocal cords from the mouth and provide a pathway to pass the ETT. Certain patient factors or abnormal upper airway anatomy can make this "line of sight" difficult to achieve, and hence the intubation difficult. In current anaesthetic practice, this situation is most likely to be managed with a videolaryngoscope (VLS). This technology incorporates a light source and optical capabilities onto the tip of a modified laryngoscope. An image is produced that can be visualised on a separate monitor. This technique is called "indirect" laryngoscopy because it does not require a direct "line of sight" to visualise the vocal cords from the mouth. It can greatly improve the visualisation of the vocal cords in most patients with a difficult intubation. Many of the devices have a sharply angled curve on their VLS blade designed for abnormal airway anatomy. This effectively allows the anaesthetist to "see around corners" and has been an extremely valuable advancement in airway management.

For the second factor, difficulty in directing the ETT, successful intubation requires the ETT to travel along the pathway between the mouth and vocal cords into the trachea.

Referring to FIG. 1, good visualisation of the vocal cords during traditional direct laryngoscopy generally implies that there is a shallow (gently curved) pathway for the ETT to follow within the oropharynx and that intubation will be easy. This however may not be the case and despite good visualisation, the ETT cannot be directed through the vocal cords.

Poor visualisation of the vocal cords during direct laryngoscopy often means that there is a more sharply angled pathway that the ETT must follow in the oropharynx. This sharp angle of approach can make it impossible to direct an ETT through the vocal cords without using a specialised introducer.

When a VLS is used to improve a poor view of the vocal cords obtained with direct laryngoscopy, it is expected that the ETT must follow a very sharply angled pathway in the oropharynx. It is generally considered essential to use an introducer to negotiate this sharp angle. This is one of the limitations of the VLS (i.e., it gives a good view of the vocal cords, but makes it more difficult to pass the ETT).

Specialized introducers are designed to guide the ETT through the vocal cords. The introducers can be bent to fit the shape of the pathway required for intubation, thus increasing the chance of successful ETT placement. There are two main types of introducer: (a) stylet or (b) bougie. The stylet is placed within the lumen of the ETT before intubation and is used as a shaper or stiffener of the ETT. It functions as a single unit combined with the ETT during intubation and is then removed after the tip of the ETT enters the vocal cords. The bougie is used as a primary device which is passed through the vocal cords into the trachea. The ETT is then slid (rail-roaded) over the bougie to enter the trachea and the bougie is then removed through the ETT lumen. It functions as a conduit for the ETT and is more versatile than a stylet. It is a very important piece of equipment used to direct the ETT through the vocal cords during a difficult intubation.

The introducers have limitations and they can fail. Referring to FIGS. 2 and 3, when an introducer has to follow a very sharp angle of approach in the oropharynx, it can be very difficult to direct the tip through the vocal cords. The introducer can be bent into the shape of this sharp approach angle, however two force vectors need to be considered in determining successful placement. Force is applied along the longitudinal vector of the shaft of the introducer which needs to be transmitted to a vector plane aligned with the tip towards the vocal cords so it can advance. There is a certain oropharyngeal approach angle beyond which the force applied along the longitudinal vector will be unable to advance the tip in its required vector (i.e., pushing the introducer from the shaft will not advance a sharply bent distal tip through the vocal cords).

If an introducer is successfully directed through the vocal cords after following a sharp angle of approach, it can then become stuck against the anterior wall of the trachea immediately below the vocal cords. The lumen of the trachea follows another acute angle away from the approach direction of the introducer at the vocal cords. This can make it very difficult to direct the introducer or ETT into the trachea despite passing through the vocal cords. (See FIG. 5.) This can also result in a failed intubation. Some of the commonly used bougies have an anteriorly angulated "coude" tip (which is recommended) however this can increase the chance of becoming stuck against the anterior tracheal wall as described above when there is a sharp approach angle.

The more difficult it is to visualise the vocal cords and the sharper the approach angle to the vocal cords means it is more difficult to successfully use an introducer. The VLS is particularly susceptible to this type of failure in a difficult intubation scenario due to its non-"line of sight" view. A well recognised and commonly reported cause of difficult or failed intubation when using a VLS involves failure to direct the ETT or introducer into the vocal cords despite good visualisation. (See FIG. 4.)

Accordingly, there exists a need to provide an improved device less prone to problems such as those described above. The present invention seeks to lessen these problems by providing a device which allows the intubation of a patient without significant difficulties associated with conventional devices.

It will be clearly understood that, if a prior art publication is referred to herein, this reference does not constitute an admission that the publication forms part of the common general knowledge in the art in Australia or in any other country.

SUMMARY

In one preferred aspect, the present invention is directed to a bougie with an adjustable distal tip. It preferably has a distal spring that facilitates movement of the distal tip. The movement is controlled by an internal wire connecting the spring to a proximal cap on the bougie. By pulling the cap off the bougie a short distance, a longitudinal force applied to the wire in a proximal direction bends the spring. This moves the bougie tip up to 90 degrees in an anterior plane. When the cap is released, the bougie tip (and spring) returns to its original neutral position by using the stored elastic energy of the spring.

It is preferably designed to handle like an existing bougie combined with a laryngoscope or VLS. The bougie tip can be flexed upwards and directed into the vocal cords when there is a sharp oropharyngeal approach angle (FIGS. 10 and 11). The tip also has the ability to passively flex downwards when passing through the vocal cords to avoid catching on the anterior tracheal wall (FIGS. 12 and 13). It therefore has two planes of movement which can assist passage through a difficult or sharply angled oropharynx. It also has the potential to reduce airway trauma due to the shock absorbing properties of the spring.

It is easy to use and will be easy to learn with many features of the existing bougies. It preferably retains all of the properties of a traditional bougie including the ability to railroad or exchange an ETT without removing the bougie from the trachea.

When there is a sharp approach angle in the oropharynx, the invention is initially inserted like a conventional bougie during laryngoscopy. The flexible shaft can be angled or bent to match the shape of the oropharyngeal passage and the tip directed towards the vocal cords by advancing the shaft in a distal direction. As the distal tip of the bougie approaches the vocal cords, the proximal cap is pulled proximally (approximately 1 cm) by an assistant (e.g., nurse, technician, anaesthetist, surgeon or other critical care physician). This flexes the distal bougie tip in an anterior direction to line up with the vocal cords. Further advancement of the shaft distally will allow the distal bougie tip to pass through the vocal cords into the trachea.

The present invention in one preferred aspect provides for a device for use with an endotracheal tube. The device includes a shaft having a proximal end, a distal end, a length from the proximal end to the distal end, a central longitudinal axis through the proximal and distal ends, and a wall from the distal end to the proximal end, the distal end including a tip. The wall forms a passage with a length from the distal end towards the proximal end, the wall including a flexible region proximate the tip. The wall outside of the flexible region both distally and proximally of the flexible region is of a stiffness greater than the flexible region, a majority of the length of the shaft being configured to fit within the endotracheal tube. The device further includes a cord having one end attached to an interior portion of the wall; and a handle operationally attached to another end of the cord for pulling the cord distally to move the tip away from the central longitudinal axis of the shaft, the cord extending along a majority of the length of the passage.

In another preferred aspect, the present invention provides for a device for use with an endotracheal tube. The device includes a shaft having a proximal end, a distal end, a length from the proximal end to the distal end, a passage, and a central longitudinal axis through the proximal and distal ends, the distal end including a tip and a spring proximate the tip, the spring having a leading end oriented toward the tip, the spring having a trailing end oriented toward the proximal end. The leading end of the spring is spaced from the distal-most portion of the tip by at least a distance greater than the maximum inner diameter of the spring, a majority of the length of the shaft being configured to fit within the endotracheal tube. The device further includes a cord having one end attached to the passage; and a handle operationally attached to another end of the cord for pulling the cord distally to move the tip away from the central longitudinal axis of the shaft, the cord extending along a majority of the length of the passage.

In a further preferred aspect, the present invention provides a method for introducing an endotracheal tube through the vocal cords and into the trachea of a patient, the trachea having an entrance and a central longitudinal axis. The method includes advancing a portion of a distal end of a bougie towards the vocal cords of the patient, the distal end including a tip and a flexible region; retracting a portion of the flexible region which moves the distal tip in an anterior or upwards direction further towards the vocal cords (as visualised during laryngoscopy or videolaryngoscopy) until the tip is in a direction generally parallel to the central longitudinal axis of the trachea; advancing the distal end of the bougie into the trachea after the tip is generally parallel to the central longitudinal axis of the trachea; and maintaining the bougie in place while guiding an endotracheal tube over the bougie to insert the endotracheal tube into the patient.

In an additional preferred aspect, the present invention provides a method for introducing an endotracheal tube through the vocal cords and into the trachea of a patient. The method includes advancing a portion of a distal end of a bougie towards the vocal cords of the patient, the distal end including a tip and a flexible region; retracting, with a single hand, a portion of the flexible region in a first direction which moves anteriorly and upwards further towards the vocal cords while directing the tip in a second direction generally opposite to the first direction (e.g., posteriorly and downwards in the plane of the longitudinal axis of the trachea); advancing, with the single hand, the distal end of the bougie into the trachea after the tip is generally in the second direction; and maintaining the bougie in place while guiding an endotracheal tube over the bougie to insert the endotracheal tube into the patient.

It is to be understood that both the foregoing general description and the following detailed description are exemplary and explanatory only and are not restrictive of the invention, as claimed. In the present specification and claims, the word "comprising" and its derivatives including "comprises" and "comprise" include each of the stated integers, but does not exclude the inclusion of one or more further integers. As used herein, "proximal" is illustrative of a portion closer to an intended user, from the user's perspective, while "distal" is illustrative of a portion away from the intended user.

The claims as filed and attached with this specification are hereby incorporated by reference into the text of the present description.

The accompanying drawings, which are incorporated in and constitute a part of this specification, illustrate several embodiments of the invention and together with the description, serve to explain the principles of the invention.

BRIEF DESCRIPTION OF THE FIGURES

FIG. 4 is a partial cross-sectional side view of a conventional bougie being used with a videolaryngoscope resulting in a failed intubation.

FIG. 4B is a partial front elevation view of the tip of the bougie of FIG. 4 showing the image that would be viewed on the videolaryngoscope screen.

FIG. 5 is a partial cross-sectional side view of a conventional bougie with a coude tip stuck against the anterior wall of the trachea after passing through the vocal cords.

FIG. 6 is a partial cross-sectional side view of a bougie in accordance with a preferred embodiment of the present invention.

FIG. 7 is a partial top plan view of the bougie of FIG. 6.

FIG. 8 is a partial cross-sectional side view of the bougie of FIG. 6 in a flexed position.

FIG. 9 is a partial top plan view of the bougie of FIG. 6 in a flexed position with an "S" shape.

FIG. 10 is a partial cross-sectional side view of the bougie of FIG. 6 being inserted into a patient in accordance with a preferred method of the present invention.

FIG. 11 is a partial cross-sectional side view of the tip of the bougie of FIG. 6 entering the trachea in accordance with the method of FIG. 10, when used with a videolaryngoscope.

FIG. 11A is a partial front elevation view of the tip of the bougie of FIG. 6 used in FIG. 11 showing the image that would be viewed on the videolaryngoscope screen.

DETAILED DESCRIPTION OF THE DRAWINGS

Figure 1:
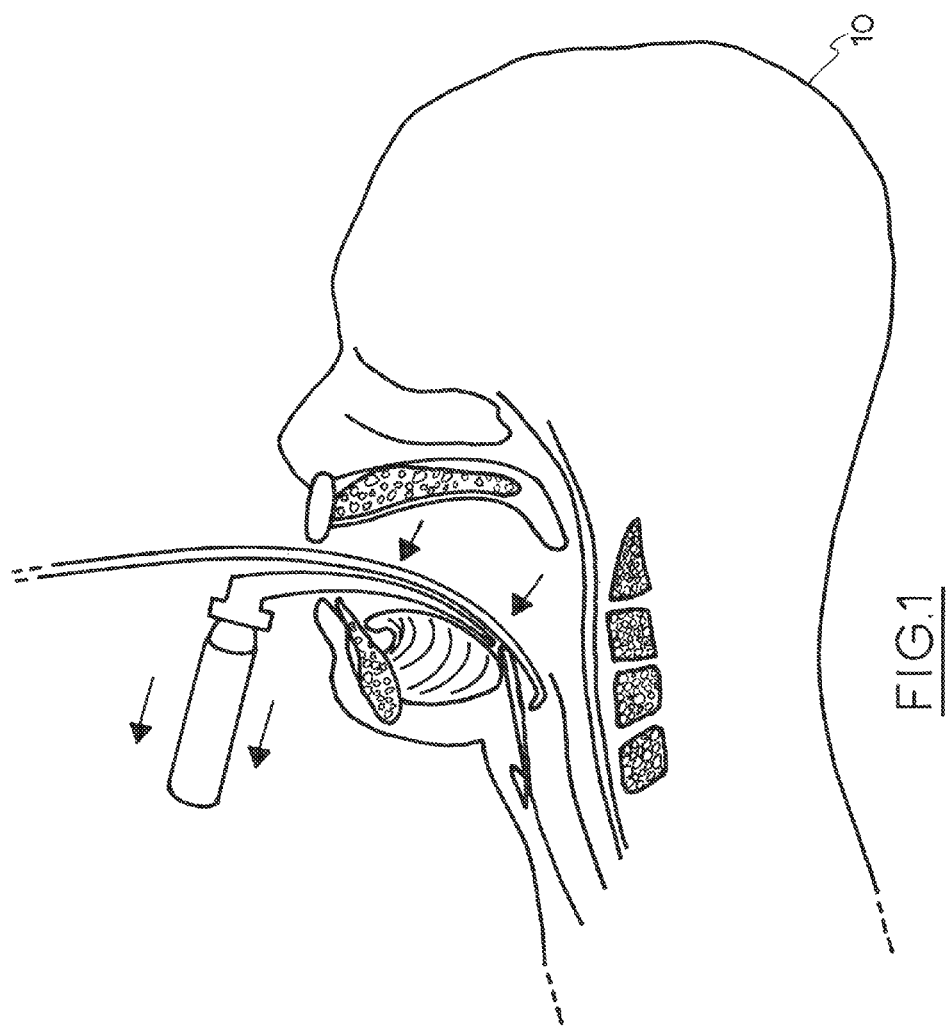
FIG. 1 is a partial cross-sectional side view of a conventional bougie being used with a standard laryngoscope.
Figure 2:
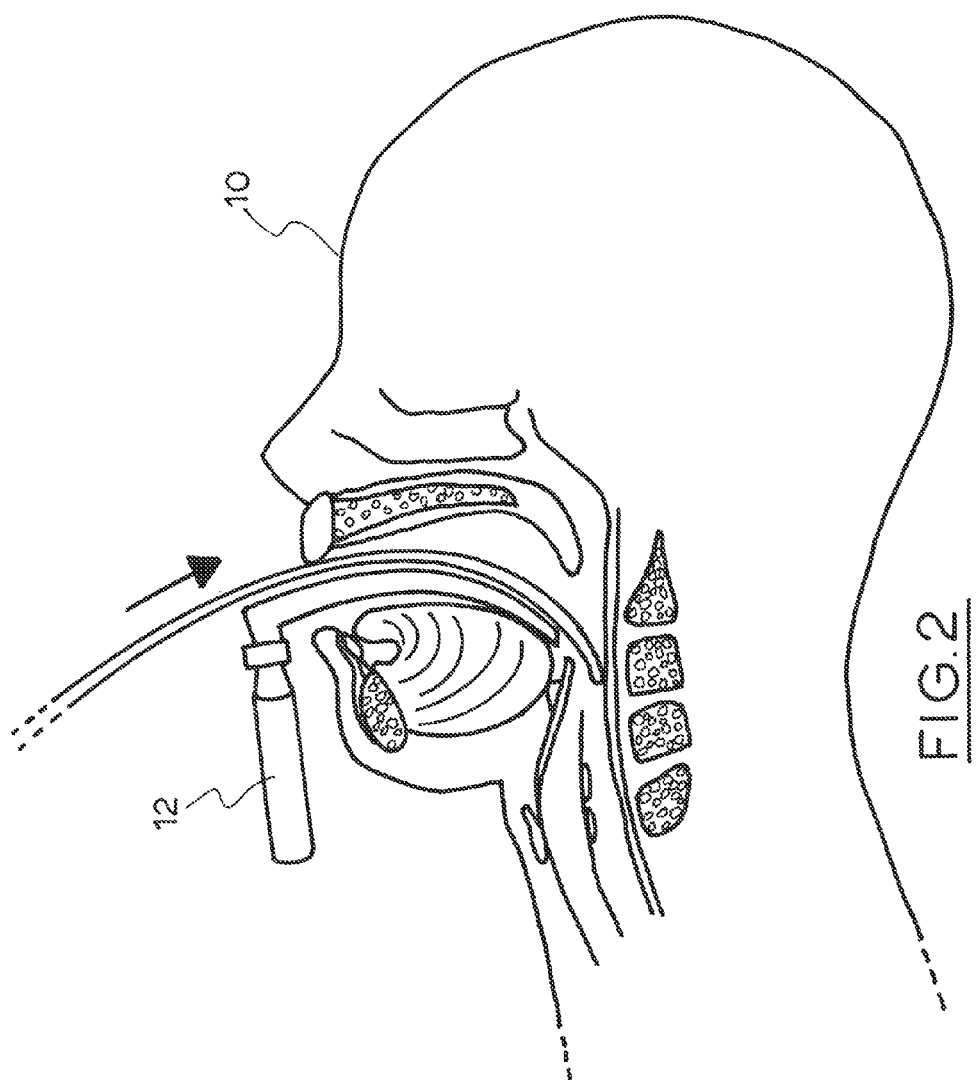
FIG. 2 is a partial cross-sectional side view of an attempt to direct a tip of a conventional bougie through the vocal cords using a standard laryngoscope.
Figure 3:
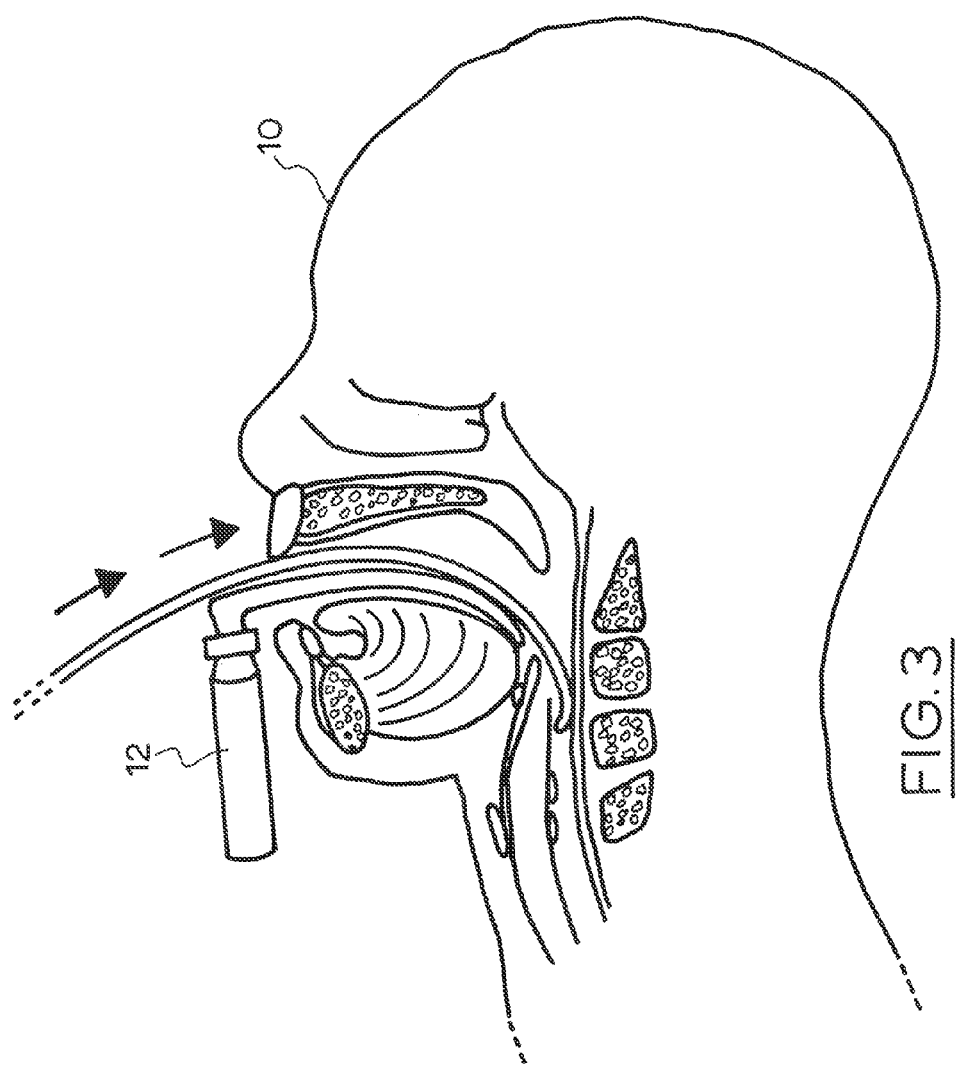
FIG. 3 is a partial cross-sectional side view of the further progression of the attempt of FIG. 2.

Reference will now be made in detail to the present preferred embodiments of the invention, examples of which are illustrated in the accompanying drawings.

FIGS. 6-13 show a preferred embodiment of a bougie 100 having a shaft 102 with a spring 104, a cap 106 at one end thereof, and a cord 108 connected to cap 106 for moving a distal portion of the bougie. In use, a user pulls cap 106 proximally to retract cord 108, which is preferably attached to a portion of the interior of spring 104. Movement of the distal portion of the bougie preferably occurs in two directions, the first and primary movement being active, and the secondary movement being passive and generally in a direction opposite to that of the primary movement. Active movement of a portion of spring 104 anteriorly moves the distal bougie tip in the same primary direction towards the vocal cords. Passive movement of the distal part of spring 104 allows the distal tip of shaft 102 to then move in a secondary direction, opposite to that of the first primary active movement. This secondary passive movement brings the distal bougie tip in line with the longitudinal axis of the trachea and enhances control and insertion of the bougie into difficult passages such as the trachea, especially when a sharp or acute oropharyngeal approach angle occurs (i.e., with a VLS used for a difficult airway). The preferred elements of bougie 100 and their interrelationship are described below.

Referring to FIGS. 6-9, bougie 100 includes shaft 102 having a proximal end 110, a distal end 112, and a wall 114 from proximal end 110 to distal end 112. Wall 114 preferably forms a passage 116 having a length from distal end 112 towards proximal end 110. Distal end 112 preferably includes a tip 118 configured for entry into an airway of a patient. Wall 114 includes a preferably resiliently flexible region, preferably in the form of spring 104, proximate tip 118.

As shown in FIGS. 6 and 7, spring 104 has a leading or distal end 120, a trailing or proximal end 122, and an interior portion 124 which preferably forms a portion of the interior of passage 116. Preferably, leading end 120 of spring 104 is spaced from the distal-most portion of tip 118, more preferably by at least a distance greater than the maximum inner diameter of spring 104. Spacing the spring from the distal point of the tip advantageously enhances the ability of bougie 100 to move in more than one direction when used to navigate through difficult passages, as will be described in further detail below. Referring again to FIG. 6, preferably a portion of wall 114 outside of spring 104, both distally and proximally of spring 104, is of a stiffness greater than that of spring 104. Preferably, the portion of the wall outside of spring 104, both distally and proximally of spring 104, is made of the same material.

Referring to FIGS. 6 and 7, bougie 100 preferably includes a retracting means to move the distal portion of the bougie. Preferably, the retracting means includes cord 108 connected to cap 106 at one end thereof, and connected to spring 104 at another end thereof. It will be appreciated that other retracting means may be used, such as spring mechanisms, and that the cord embodiment described below is exemplary only. Continuing with reference to FIGS. 6 and 7, cord 108 includes a proximal end 126 connected to cap 106, and a distal end preferably attached to a portion of passage 116. More preferably, the distal end of cord 108 is attached to interior portion 124 of spring 104. As shown in FIG. 7, the distal end of cord 108 is preferably attached to interior portion 124 at more than one location, more preferably, at least two locations. Thus, the distal end of cord 108 preferably includes a first distal wire 128 and a second distal wire 130 for attachment to two different, spaced-apart first and second attachment points 132, 134, respectively, within passage 116. Attachment points 132, 134 are preferably spaced-apart from one another in the range of 90 to 180 degrees relative to the central longitudinal axis of the shaft. It will be appreciated that two wires may be used to connect to cap 106, run internally through substantially the entire length of the shaft 102, pass through guide 136 and then branch to connect to the attachment points 132 and 134.) First attachment point 132 and second attachment point 134 are preferably located proximal of leading end 120 of spring 104, more preferably in a distal half of spring 104, and most preferably, closer to leading end 120 than trailing end 122 of spring 104. First distal wire 128 and second distal wire 130 preferably pass through a guide 136 and are connected to cap 106. Guide 136 is preferably attached to a portion of passage 116. Positioning the attachment points of the cord proximally of the leading end of the spring advantageously enhances the ability of bougie 100 to move in more than one direction when used to navigate through difficult passages, as will be described in further detail below.

Referring to FIGS. 6-9, cap 106 is preferably configured for gripping by a user to retract or pull cord 108 to move the distal portion of bougie 100. Cap 106 may be shaped in a variety of ways in order to suit the needs of the user. It will be appreciated that a retraction mechanism other than a cord and cap may be used to move the distal portion of the bougie. For example only, the proximal portion of the bougie may include a retractable, spring-loaded handle so that the user may squeeze a trigger to move the distal portion of bougie 100.

As shown in FIGS. 6 and 7, bougie 100 preferably includes a sleeve 138 of a thin, pliable medical grade plastic coating to externally cover spring 104 and a portion of the wall of shaft 102 on either side of spring 104.

Preferred dimensions are set forth below, although it will be appreciated that the dimensions may be varied as suitable for the intended application. Shaft 102 is preferably in the range of 60-80 cm, more preferably 70 cm in length. Shaft 102 preferably has an outer diameter in the range of 4.0 to 5.0 mm, more preferably 4.5 mm. Tip 118 preferably has a length in the range of 20-30 mm, while cap 106 preferably has a length in the range of 10-20 mm. It will be appreciated that the dimensions above may be modified for use in paediatric applications as desired.

Spring 104 preferably has a length along its central longitudinal axis in the range of 20-40 mm, with a preferred outer diameter of 4.6-4.8 mm. Preferably the outer diameter of spring 104 is equal to the outer diameter of shaft 102 so that the bougie has a uniform dimension throughout its length.

Sleeve 138 preferably has a length sufficient to cover spring 104 and a portion of the wall on either side of the spring. For example, sleeve 138 preferably has a length in the range of 30-60 mm. It will be appreciated that sleeve 138 may be modified to extend the entire length of the bougie if desired.

First wire 128 and second wire 130 preferably each have a diameter of approximately 0.3 mm. First attachment point 132 and second attachment point 134 each are preferably located approximately 5-10 mm from leading end 120 of spring 104. The attachments of first wire 128 and second wire 130 from 5-10 mm from the leading end of spring 104 allow tip 118 to move in a secondary plane opposite to that caused by the wire tension. This allows the tip of bougie 100 to be actively moved in an anterior/dorsal plane by the wire, but then move passively posteriorly as it contacts with the anterior wall of the trachea (described in further detail below). This results in a "S" shape as shown in FIG. 9, and preferably prevents the distal tip from becoming stuck against the anterior wall of the trachea as it passes through the vocal cords at a sharp approach angle. It will be appreciated that these dimensions are representative only and may be varied as appropriate. Additionally, the ranges described above may include a subset of ranges therein without departing from the scope of the present invention.

Having described the preferred components of bougie 100, a preferred method of use will now be described with reference to FIGS. 10-13. Referring to FIGS. 10 and 11, an anaesthetist inserts a standard laryngoscope (FIG. 10) or preferably a videolaryngoscope (FIG. 11) into the patient. The initial position of bougie 100 is preferably in a neutral position with cap 106 sitting at the end of shaft 102. In the initial position, there is preferably no tension on the cord, and the spring and distal tip are in straight alignment with the rest of the shaft. Thereafter, the anaesthetist inserts bougie 100 into the patient, preferably through an airway passage such as the mouth. Once the distal portion of bougie 100 has entered the patient, a portion of the distal end of bougie 100 is advanced towards the vocal cords of the patient as shown in FIGS. 10 and 11. In order to facilitate the procedure, an image 140 (FIG. 11A) of the upper airway may preferably be obtained using video laryngeal scope 12. Preferably, the image is obtained proximate the tip while the distal portion of the bougie is within the patient.

The image obtained from the imaging device proximate the tip (such as video laryngeal scope 12) may be viewed on a separate screen connected to the device by a wired or wireless mechanism. The imaging screen may include a smart phone and utilize a smart phone application.

Continuing with reference to FIG. 11, a portion of spring 104 is retracted, preferably by pulling cap 106. The pulling of cap 106 results in a primary movement of the distal spring/flexible tip away from the central longitudinal axis of the bougie shaft and towards the vocal cords and into the trachea. This actively moves the bougie tip in a primary direction, anteriorly, up and towards the vocal cords.

Figure 12:
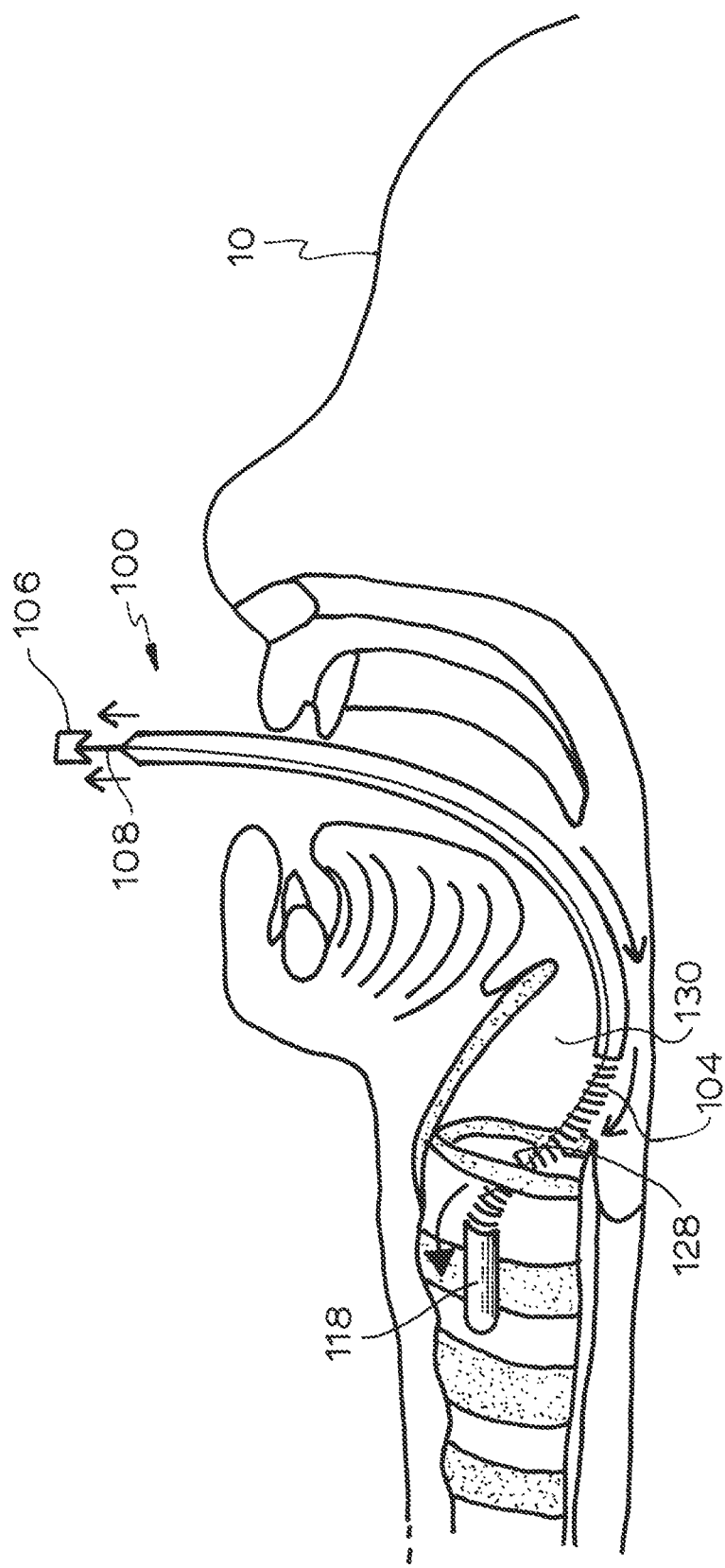
FIG. 12 is a partial cross-sectional side view of the tip of the bougie of FIG. 6 sliding down the trachea in accordance with the method of FIG. 10.

Referring to FIG. 12, after the bougie tip passes through the vocal cords into the trachea, tip 118 passively moves in a secondary direction, posteriorly, down and away from the vocal cords to lie in a direction generally parallel to the central longitudinal axis of the trachea. Preferably, the spring portion is retracted when the anaesthetist or their assistant pulls on cord 108 using cap 106 attached at the end of the cord. The longitudinal tension on cord 108 caused by the pulling on the cap is transmitted to spring 104, which shortens on its dorsal surface. This causes the spring and the distal tip of the bougie to bend in a dorsal direction up to 90 degrees. The attachments of first distal wire 128 and second distal wire 130 proximal of the leading end of the spring and within the spring facilitate movement of the distal tip of the bougie in a secondary plane opposite to that caused by the wire tension. This permits tip 118 to be actively moved in an anterior/dorsal plane by cord 108, but then move passively posteriorly as it contacts with the anterior wall of the trachea. This results in a "S" shape and helps to prevent the distal tip from becoming stuck against the anterior wall of the trachea as it passes through the vocal cords, especially if this passage through the vocal cords occurs at a sharp angle.

Figure 13:
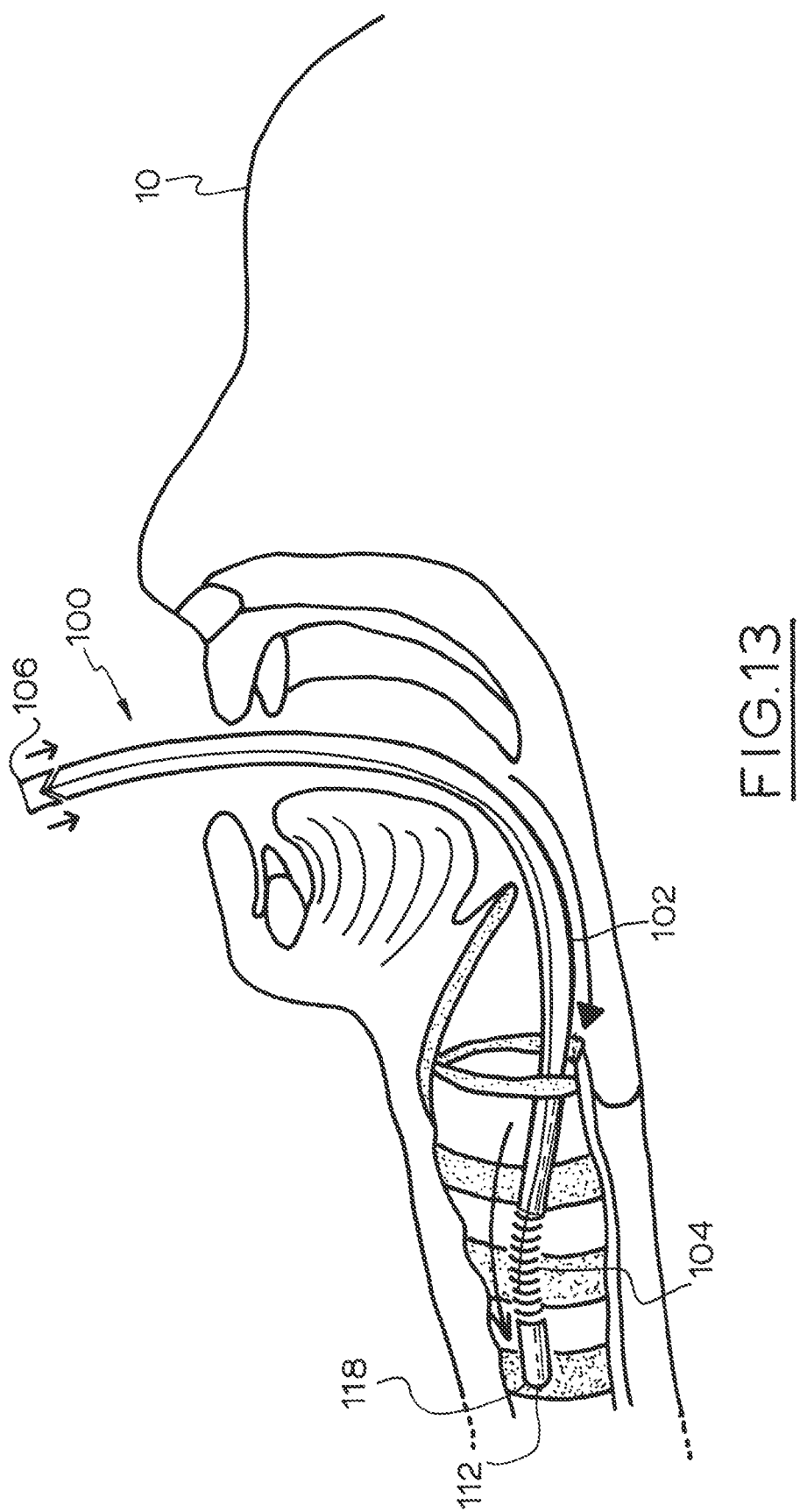
FIG. 13 is a partial cross-sectional side view of the tip and shaft of the bougie of FIG. 6 inserted in the trachea in accordance with the method of FIG. 10.

Referring to FIG. 13, when cap 106 is released, the longitudinal tension on the wire will be released and spring 104 will return to its original neutral position using the elastic energy gained when bent (compressed on the dorsal side). This passive recoil of the spring returns distal tip 118 to its neutral position and cap 106 moves back to sit on the proximal part of shaft 102 of bougie 100. Distal end 112 of bougie 100 is advanced into the trachea after tip 118 is generally parallel to the central longitudinal axis of the trachea. Thereafter, bougie 100 is maintained in place while an endotracheal tube is guided over the bougie to insert the endotracheal tube into the patient. The bougie is then removed from within the ETT by pulling it out proximally and the ETT preferably remains in place to be used for ventilation of the patient.

Preferably, the primary procedure is conducted by the anaesthetist without the need of an assistant. For example, after the tip of the bougie has been advanced towards the vocal cords, the anaesthetist, using a single hand, retracts a portion of the spring to actively move the bougie tip in its primary direction anteriorly, up and towards the vocal cords. Once the bougie tip is guided through the vocal cords into the trachea, the distal spring and bougie tip may passively move in its secondary direction, posteriorly, down and away from the vocal cords to lie in a direction parallel with the central longitudinal axis of the trachea. Thereafter, the distal end of the bougie is advanced, using the single hand, deeper into the trachea after the tip is generally in the second direction. Alternatively, it is equally feasible to use the assistant that is normally required for use of the traditional bougie during intubation and railroading of the ETT.

It will be appreciated that the steps described above may be performed in a different order, varied, or some steps added or omitted entirely without departing from the scope of the present invention. For example, an airway introducer incorporating a flexible region in the form of a spring such as described above may be used for other procedures, and used through other passages where internal navigation is difficult. Examples include navigation of airway passages such as the nasal passage, other procedures such as a colonoscopy, and/or procedures where artificial insertions are made (e.g., laparoscopic procedures), and a tip of a surgical instrument is required to be configured to navigate around difficult areas.

Figure 14:
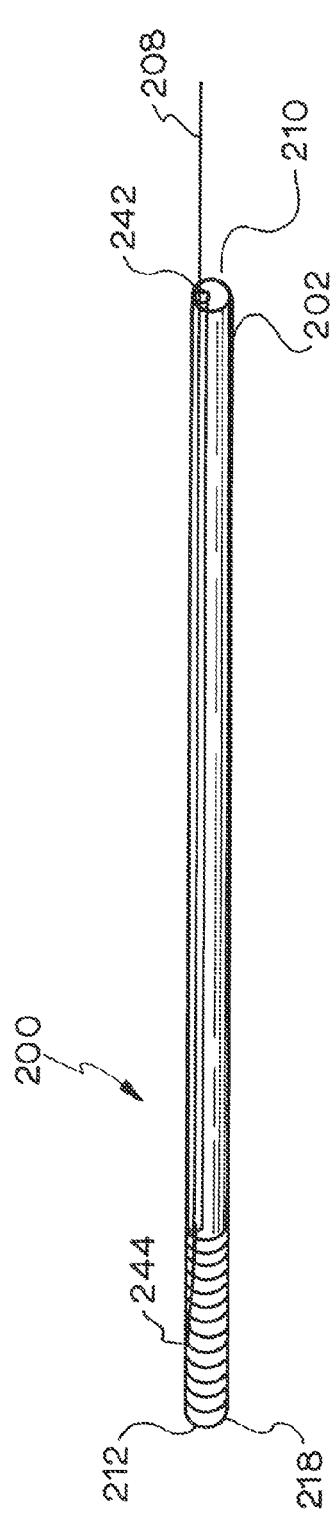
FIG. 14 is a partial cross-sectional side view of a bougie in accordance with another preferred embodiment of the present invention.
Figure 15:
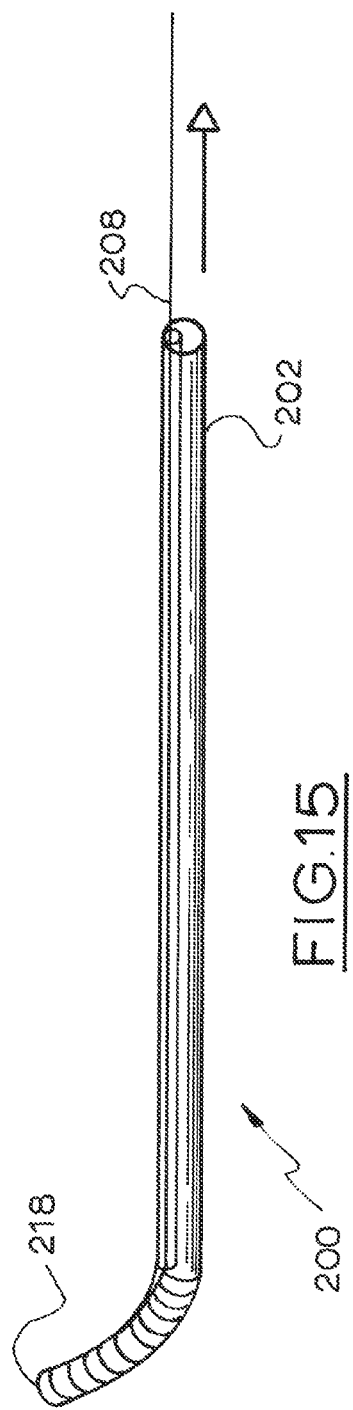
FIG. 15 is a partial cross-sectional side view of the bougie of FIG. 14 in a flexed position.

FIGS. 14 and 15 show another embodiment of a bougie 200, which is similar to bougie 100 except that bougie 200 includes an internal lumen 242 sized and configured for pull wire 208 to pass therethrough along a substantial portion of the length of bougie 200. Wire 208 is attached distally of distal end 212 at a single attachment point 244. Another difference is that the flexible region is formed as a series of corrugations at distal end 212. The corrugations are preferably integrally formed of the same material from a single mold, but vary in thickness. The flexible region may also be formed by the same material of the shaft, but comprising a lesser durometer. The operation of bougie 200 is similar to that of bougie 100 described above.

The foregoing description is by way of example only, and may be varied considerably without departing from the scope of the present invention. For example only, the shape of the tip may be varied as a blunt tip and/or a straight or coude tip or reverse coude tip. The flexible region may be configured as a spring as set forth above, or may be a flexible, unitary structure having a series of corrugations. Where the flexible region is corrugated, it may be made from the same material as the remainder of the shaft. If desired, where a spring is utilised, it may be made from the same material as the shaft, and may be formed from a non-metallic material, such as a medical grade plastic having sufficient resilience and stiffness qualities to function in a spring-like manner.

The flexible region may be manufactured without a spring if desired. For example only, the shaft may be formed with multiple layers, each layer being of differing length and flexibility or stiffness. As one example, the flexible region may be formed with a soft inner plastic layer and a harder outer coating layer (e.g., "jacket"). The softer, inner layer may have a length longer than that of the harder outer layer. The stiffer outer sheath layer provides rigidity for the main shaft to be held, shaped and directed, and the inner softer layer that preferably protrudes can be flexed, steered or directed by a guidance system such as a wire, which facilitates navigation through an angled airway pathway. As another example, the distal flexible region may not have a separate distal tip composed of a different material to that of the flexible region. The material forming the distal flexible segment, whether this be a spring or other flexible material, may extend all the way to and terminate at the distal tip of the bougie.

When using multiple layers, each layer may include one or more features to promote different degrees of stiffness. For example, in addition to, or in place of different lengths, each layer may have a different thickness, include an embedded supporting structure, such as wire braiding or monofilament (with different wire configurations such as single, double or ribbon), and/or be made from a different material relative to another layer. Each layer may be manufactured with a variable stiffness along its length. A few benefits of encapsulating a wire braiding in a layer include better torque control and the ability to form a softer distal portion into a variety of curves, and kink resistance.

The shaft may include multiple lumens if desired. For example, the shaft may form a single, main lumen, with one or more smaller lumens extending along the interior of the shaft. Any interior lumens may be of differing diameter, shape and length relative to each other and/or to the length of the shaft. One or more of the lumens may be configured for a navigation control, such as a wire or guide wire to assist in directing the tip of the bougie. Instead of, or in addition to using a wire or guide wire, the navigation control may utilise a smaller diameter stiff tube with a highly lubricated outer coating (e.g., Teflon) located within a smaller dorsal lumen within the bougie. The stiff internal tube functions like a wire and is preferably attached to the distal tip (at a variable distance from the distal tip similar to that described above for the spring). The stiff internal tube is preferably configured to travel through the dorsal lumen to the proximal end of the bougie, where it is preferably configured to protrude and be grasped or pulled proximally. It will be appreciated that the proximal end of the stiff internal tube may be configured in a variety of ways for engagement by a user to move the internal tube. It will be further appreciated that the stiff internal tube may be solid if desired. The distal end of the internal tube may be curved or shaped to engage a similarly shaped portion of an internal lumen for better navigation if desired.

The retraction mechanism preferably includes a cord formed as a metallic wire. However, the cord may be formed from other materials such as a textile or plastic if desired. The retraction mechanism may utilise a spring, or other "spring-like" mechanisms as desired, which may be configured for engagement with a trigger mechanism. Where the cord includes a plurality of wires, a guide may be included proximally of the flexible region (such as shown in FIG. 6). Grooves may be included in the interior surface of the passage to facilitate guiding one or more wires during movement of the tip. Preferably, no portion of the wire travels outside of the interior of the shaft while the shaft is in the patient. Travel of a wire outside the shaft while it is in the patient increases the risk of damage to delicate tissue structures.

The bougie may be modified with a variety of retraction mechanisms. For example only, a retractable pen-type mechanism may be utilised, similar to a retractable click pen mechanism utilizing a modified cam and spring mechanism. Attached to the proximal shaft of the bougie is a button that can be clicked. The button is attached to a cam mechanism that moves when the button is clicked up and down. An internal wire attached to the distal bougie tip (with its distal flexible spring mechanism) is attached to the proximal button "click-cam" mechanism. A second spring is coupled to the "click-cam" mechanism in a location within the bougie shaft proximate to the distal spring used for moving the bougie tip. This second spring is preferably used as a tensioning device attached to the wire to facilitate retraction when the proximal button is clicked in or out. The neutral position of the button may be the opposite to that of the click pen (i.e., button depressed down in the "pen open" position is neutral, and the button clicked up in the "pen closed" position facilitates the active retraction of the wire which moves the distal tip).

Another retraction mechanism may include a shaft bending mechanism. For example, bending part of the shaft proximate to the distal spring mechanism retracts an internal wire connected to the distal bougie tip. The internal wire is connected to the internal shaft of the bougie at a point proximate to the shaft bending point. The shaft bending point may include a second spring or a corrugated section, or include a section of bougie more flexible than the rest of the shaft. Bending of the shaft results in retraction of the internal wire that is connected to the distal flexible mechanism and results in movement of the bougie tip away from the central longitudinal axis of the bougie.

A further exemplary retraction mechanism may include a shaft sliding mechanism. For example, a slide mechanism is located in the shaft of the bougie proximate to the distal spring mechanism. The internal wire attached to the distal spring mechanism is connected proximally to the slide mechanism on its internal surface. The slide is located on the exterior of the bougie shaft and can be slid proximally to retract the internal wire and result in movement of the distal bougie tip in a similar the shaft bending mechanism described above.

Another example of a retraction mechanism includes use of an external wire mechanism. For example, the internal wire attached distally to the flexible spring mechanism exits the shaft of the bougie to become external to the bougie shaft at a point proximate to the distal 20 cm to 30 cm of the shaft. The external position of the wire can then be pulled directly to cause retraction of the internal wire and facilitate movement of the distal bougie tip. The proximal part of the external wire is preferably attached to the exterior of the bougie shaft proximate to its exit point.

The mechanism of controlling movement of the distal flexible region may involve an automated process. This automation may involve the use of a micromotor or micromotion system configured to fit within the internal shaft of the device (for example a longitudinal squiggle or vibration motor) coupled to an internal wire that produces torque and movement of the distal tip. This motorised mechanism may be powered by DC batteries (for example SR416SW batteries) or an external power source (e.g., USB). The automated mechanism may be coupled to an optical imaging device and controlled by an external mechanism utilizing the imaging screen of the optical device in a wired or wireless mechanism. This mechanism may include using a smart phone which may utilize a smart phone application.

The cap may be replaced with a trigger such as described above. It will be appreciated that the cap may be formed in a variety of ways to enable an anaesthetist to move the distal portion of the bougie.

The features described with respect to one embodiment may be applied to other embodiments, or combined with or interchanged with the features of other embodiments, as appropriate, without departing from the scope of the present invention.

The present invention in a preferred form provides an advantage of enhanced tip navigation with multi-directional movement, which lends itself to use in airway intubation or other medical or surgical procedures where difficult passages must be traversed. Another advantage is its ease of use. For example, a single person may use the instrument in one embodiment, or in another embodiment it is an easy manoeuvre for an assistant or second person to pull the cap. Conventional navigation instruments often require more than one person and it is usual to have an assistant when using a traditional bougie for a difficult intubation to railroad the ETT over the bougie.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for use with an endotracheal tube, said device comprising:
    a shaft having a proximal end, a distal end, a length from said proximal end to said distal end, a central longitudinal axis through said proximal and distal ends, and a wall from said distal end to said proximal end, said distal end including a tip, said wall forming a passage with a length from said distal end towards said proximal end, said wall including a flexible region devoid of ridges and protuberances, said wall outside of said flexible region being of a stiffness greater than said flexible region, a majority of the length of said shaft being configured to fit within an endotracheal tube;
    a cord having a first end portion coupled to said wall; and
    a handle operationally attached to a second end portion of said cord for pulling said cord distally to move said tip away from the central longitudinal axis of said shaft.

2. The device of claim 1, wherein said flexible region has a rest configuration and is resiliently flexible such that when a force that causes the flexible region to deform from the rest configuration is removed, said flexible region returns to said rest configuration.

3. The device of claim 2, wherein said flexible region includes a spring.

4. The device of claim 2, wherein, a flexible portion of said wall has a varying thickness such that said flexible portion of said wall forms corrugations.

5. The device of claim 1, wherein said first end portion of said cord includes a first distal branch and a second distal branch, said first distal branch coupled to said wall at a first attachment point, said second distal branch coupled to said wall at a second attachment point.

6. The device of claim 5, wherein said first attachment point is spaced 90 to 180 degrees relative to the central longitudinal axis from said second attachment point.

7. A device for use with an endotracheal tube, said device comprising:
    a shaft having a proximal end, a distal end, a length from said proximal end to said distal end, a passage, and a central longitudinal axis through said proximal and distal ends, said distal end including a tip and an elastically deformable portion, said elastically deformable portion having an exterior surface devoid of ridges and protuberances, said elastically deformable portion having a leading end oriented toward said tip, said elastically deformable portion having a trailing end oriented toward said proximal end, said leading end of said elastically deformable portion being spaced from the distal-most portion of said tip by at least a distance greater than the maximum inner diameter of said elastically deformable portion, a portion of the length of said shaft being configured to fit within an endotracheal tube;

a cord having a first end portion coupled to said passage; and a handle operationally attached to a second end portion of said cord for pulling said cord distally to move said tip away from the central longitudinal axis of said shaft, said cord extending along a majority of the length of said passage.

8. The device of claim 7, wherein said first end portion of said cord is coupled to an interior portion of said elastically deformable portion.

9. A method for introducing an endotracheal tube comprising:

advancing a portion of a distal end of a bougie towards the vocal cords of a patient, the bougie including:

a shaft having a proximal end, a distal end, a length from said proximal end to said distal end, a central longitudinal axis through said proximal and distal ends, and a wall from said distal end to said proximal end, said distal end including a tip, said wall forming a passage with a length from said distal end towards said proximal end, said wall including a flexible region devoid of ridges and protuberances, said wall outside of said flexible region being of a stiffness greater than said flexible region, a majority of the length of said shaft being configured to fit within an endotracheal tube;

a cord having a first end portion coupled to an interior portion of said wall; and a handle operationally attached to a second end portion of said cord for pulling said cord distally to move said tip away from the central longitudinal axis of said shaft.

10. The method of claim 9, further comprising:

actuating the handle to retract a portion of the cord causing the tip to actively move in a primary direction, anteriorly, up and towards the vocal cords;

guiding the tip through the vocal cords to enter the proximal trachea while the tip remains in its actively retracted position;

returning the retracted portion of the cord to cause the tip to move towards the central longitudinal axis of the trachea;

advancing the distal end of the bougie deeper into the trachea after returning retracted portion of the cord; and maintaining the bougie in place after advancing the distal end of the bougie deeper into the trachea while guiding an endotracheal tube over the bougie to insert the endotracheal tube into the patient.

11. The method of claim 10, wherein actuating the handle includes actuating the handle with a single hand, the method further comprising:

guiding, with the single hand, the tip through the vocal cords to enter the proximal trachea while it remains in its actively retracted position;

returning, with the single hand, the retracted portion of the cord to cause the tip to move towards-the central longitudinal axis of the trachea;

advancing, with the single hand, the distal end of the bougie deeper into the trachea after returning the retracted portion of the cord; and maintaining the bougie in place while guiding an endotracheal tube over the bougie to insert the endotracheal tube into the patient.

12. The method of claim 11, further comprising railroading said endotracheal tube over said bougie.

13. The method of claim 12, further comprising, removing said bougie from the patient after railroading said endotracheal tube over said bougie, said endotracheal tube remaining in the patient after said bougie is removed from the patient.

14. The device of claim 1, further comprising said endotracheal tube.

15. The device of claim 1, wherein said flexible region includes a plurality of layers, a first layer from said plurality of layers including wire braiding and having a first elasticity, a second layer from said plurality of layers disposed outside said first layer, said second layer having a second elasticity different from said first elasticity.

16. The device of claim 1, wherein said flexible region is biased in a first direction such that said flexible region urges said tip of said distal end in said first direction away from the central longitudinal axis of said shaft.

17. The device of claim 16, wherein said first end portion of said cord is coupled to an interior portion of said wall such that, when said cord is pulled, said cord applies a force to said wall to urge said tip of said distal end in a second direction away from the central longitudinal axis of said shaft, said second direction different from said first direction.

18. The device of claim 1, wherein said flexible region has a first segment having a first elasticity and a second segment distal of said first segment, said second segment having a second elasticity different from said first elasticity.

19. The device of claim 1, wherein the wall has an outside surface and an inside surface, the inside surface of the wall defining an enclosed passage from said distal end to said proximal end.

20. The device of claim 1, wherein the flexible region incorporates wire braiding, wire reinforcing or embedded supporting structures into the wall of the flexible region.

21. The device of claim 19, wherein said flexible region has a first segment having a first elasticity and said flexible region has a second segment distal of said first segment having a second elasticity different from said first elasticity.

22. The device of claim 20, wherein the wall of the flexible region is comprised of a plurality of layers including at least a first layer having a first elasticity and a second layer from said plurality of layers having a second elasticity different from said first elasticity.

23. The device of claim 20, wherein said passage is a first enclosed passage, said device further comprising a second enclosed passage, the cord being disposed within said second enclosed passage.

24. The device of claim 20, wherein said passage is an enclosed passage and the cord is wholly disposed within the enclosed passage.

25. The device of claim 20, wherein the first end portion of the cord is coupled to the flexible region of the wall.

26. The device of claim 20, wherein said flexible region has a distal end and a proximal end, said first end portion of said cord is coupled to said inside surface of said wall closer to said proximal end of said flexible region than said distal end of said flexible region.

27. The device of claim 20, wherein said flexible region has a distal end and a proximal end, said first end portion of said cord is coupled to said inside surface of said wall closer to said distal end of said flexible region than said proximal end of said flexible region.

28. The device of claim 21, wherein said flexible region has a distal end and a proximal end, said first end portion of said cord is coupled to said inside surface of said wall proximate to the distal end of said flexible region such that the tip of the device flexes in a direction opposite to a direction of movement caused by pulling said cord such that the distal end flexes in an S-shape.

29. The device of claim 1, wherein said wall outside of said flexible region is a first portion of the wall outside of the flexible region, the first portion of the wall being proximal of said flexible region, said wall including a second portion of the wall outside of the flexible region, the second portion of the wall being distal of said flexible region.

30. The device of claim 29, wherein the first portion of the wall has a length greater than a length of the second portion of the wall.

31. The device of claim 29, wherein the first portion of the wall is constructed of the same material as the second portion of the wall.

32. The device of claim 29, wherein the tip includes one of a coude tip, a reverse coude tip, or a bullet tip.

33. The device of claim 7, wherein said elastically deformable portion is biased in a first direction such that said elastically deformable portion urges said tip of said distal end in said first direction.

34. The device of claim 33, wherein said first end portion of said cord is coupled to said passage such that, when said cord is pulled, said cord applies a force to said passage to urge said tip of said distal end in a second direction away from the central longitudinal axis of said shaft, said second direction opposite said first direction.

35. The device of claim 7, further comprising said endotracheal tube.

36. A device for use with an endotracheal tube, said device comprising:
  a shaft having a proximal end, a distal end, a length from said proximal end to said distal end, a central longitudinal axis through said proximal and distal ends, and a wall from said distal end to said proximal end, said distal end including a tip where at least a majority of the length of said shaft is configured to fit within an endotracheal tube;
  said wall having an outside surface and an inside surface, where said inside surface of the wall defines an enclosed passage, where the enclosed passage has a length from said distal end towards said proximal end, said wall including a flexible region having an exterior surface devoid of ridges and protuberances, said wall outside of said flexible region being of a stiffness greater than said flexible region;
  a cord having a first end coupled to a portion of said wall in the flexible region; and
  a handle operationally attached to a second end of said cord for pulling said cord to move said tip away from the central longitudinal axis of said shaft.

37. The device of claim 1, wherein the device is a bougie.

38. The device of claim 3, further comprising a sleeve disposed over the spring such that said wall including said flexible region is devoid of ridges and protuberances.

* * * * *